United States Patent [19]

Drake

[11] Patent Number: 4,579,977

[45] Date of Patent: Apr. 1, 1986

[54] PROCESS FOR THE OXIDATION OF ORGANIC HALIDES TO ORGANIC ALDEHYDES

[75] Inventor: Charles A. Drake, Nowata, Okla.

[73] Assignee: Phillips Petroleum Company, Bartlesville, Okla.

[21] Appl. No.: 684,184

[22] Filed: Dec. 20, 1984

[51] Int. Cl.$^4$ ............................................. C07C 45/27
[52] U.S. Cl. .................................................... 568/490
[58] Field of Search ......................................... 568/490

[56] References Cited

U.S. PATENT DOCUMENTS

| | | | |
|---|---|---|---|
| 2,888,488 | 5/1959 | Nace ..................................... | 568/490 |
| 4,174,352 | 11/1979 | Fisher et al. ......................... | 568/490 |
| 4,175,204 | 11/1979 | Babler ................................. | 568/490 |
| 4,335,263 | 6/1982 | Minai ................................... | 568/490 |

FOREIGN PATENT DOCUMENTS 0857104  8/1981  U.S.S.R. ............................. 568/490

OTHER PUBLICATIONS

Nace, "J. Organic Chem.", vol. 24, p. 1792.
Kornblum et al., "J. Amer. Chem. Soc.", vol. 79, p. 6562 (1957).
Ganem et al., "Tetrahedron Letters", No. 11, pp. 917-920 (1974).

Primary Examiner—Werren B. Lone
Attorney, Agent, or Firm—Stephen E. Reiter

[57] ABSTRACT

Process for the conversion of organic halides to organic aldehydes is provided wherein a mixture consisting essentially of organic halide and dimethyl sulfoxide is first heated to a temperature of about 40°-100° C. for a time in the range of about 0.1-12 hours, then sodium bicarbonate is added and thereafter the resulting mixture further heated to a temperature in the range of about 90°-180° C. for an additional time in the range of about 0.1-12 hours. In a specific embodiment of the invention, a cosolvent selected from the group consisting of dimethylphthalate, triglyme and caprolactone is added along with the sodium bicarbonate prior to the second heating step. In another specific embodiment of the invention, the second heating step is carried out under reduced pressure conditions. The formation of alcohol by-product is greatly reduced in the practice of the present invention. Thus higher yields and easier recovery of the desired aldehyde product are achieved.

10 Claims, No Drawings

PROCESS FOR THE OXIDATION OF ORGANIC HALIDES TO ORGANIC ALDEHYDES

BACKGROUND

This invention relates to oxidation reactions. In another aspect, this invention relates to the conversion of organic halides to organic aldehydes having the same number of carbon atoms. In yet another aspect, this invention relates to the reaction of primary halide compounds with dimethyl sulfoxide.

The oxidation of certain organic halide compounds with dimethyl sulfoxide (DMSO) in the presence of a non-nucleophilic base such as sodium bicarbonate, to produce organic aldehydes, is known to those skilled in the art. A problem encountered with this reaction is the undesired formation of by-product alcohol, which presumably results from the hydrolysis of the reactant halide, rather than oxidation thereof. The formation of by-product alcohol is undesirable because yields of the desired aldehyde product are thereby reduced and the resulting aldehyde/alcohol product mixtures are difficult to separate.

OBJECTS OF THE INVENTION

An object of the present invention, therefore, is a process for the conversion of organic halides to organic aldehydes wherein increased yields of the desired aldehyde product are obtained.

Another object of the present invention is a process for the conversion of organic halides to organic aldehydes wherein decreased quantities of by-product alcohol are produced.

These and other objects of the invention will become apparent from the disclosure and claims provided herein.

STATEMENT OF THE INVENTION

In accordance with the present invention, I have discovered that the amount of alcohol by-product produced when organic halides are oxidized in the presence of DMSO can be greatly reduced by first heating together a mixture of organic halide and DMSO, then adding sodium bicarbonate and further heating the resulting mixture to complete the desired reaction. By employing this procedure, the amount of alcohol by-product produced can be reduced by as much as 50% or more.

In accordance with another embodiment of the invention, I have discovered that the yield of organic aldehyde produced by oxidation of organic halide in the presence of DMSO can also be increased by employing in the oxidation reaction a co-solvent selected from the group consisting of dimethylphthalate, triglyme, and caprolactone.

In accordance with yet another embodiment of the invention, I have discovered that by carrying out the oxidation of organic halide under reduced pressure, the yield of organic aldehyde is increased while the amount of by-product alcohol formed is reduced.

DETAILED DESCRIPTION OF THE INVENTION

In accordance with the present invention, a process is provided for the conversion of organic halides to organic aldehydes comprising a first step of heating a mixture of organic halide and dimethyl sulfoxide to a temperature in the range of about 40° to about 100° C. for a time in the range of about 0.1 to 12 hours followed by a second step of adding at least one mole of sodium bicarbonate per mole of organic halide to the result of the first step and thereafter heating the sodium bicarbonate-containing mixture to a temperature in the range of about 90° to 180° C. for a time in the range of about 0.1 to 12 hours.

In accordance with another embodiment of the present invention, a process for the conversion of organic halides to organic aldehydes as hereinabove described is provided further comprising adding at least one cosolvent selected from the group consisting of dimethylphthalate, triglyme and caprolactone along with the sodium bicarbonate to the mixture which results from the first step.

In accordance with yet another embodiment of the present invention, a process for the conversion of organic halides to organic aldehydes is provided wherein a mixture of organic halide and dimethyl sulfoxide are heated as hereinabove described, then the second step of heating in the presence of sodium bicarbonate is carried out under reduced pressure.

Organic halides contemplated to be useful in the practice of the present invention can be defined broadly by the structure $RCH_2\text{-}X$, wherein R is a $C_3\text{-}C_{30}$ organic radical. Preferably, R is a $C_3\text{-}C_{30}$ hydrocarbyl radical, since the presence of other functional groups may interfere with the desired conversion reaction. Most preferably, R will be selected from a member of the alkenyl group defined by the following structure;

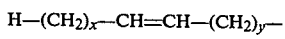
$$H\text{—}(CH_2)_x\text{—}CH\text{=}CH\text{—}(CH_2)_y\text{—}$$

so that most preferred organic halides employed in the practice of the present invention have the following formula:

$$H\text{—}(CH_2)_x\text{—}CH\text{=}CH\text{—}(CH_2)_y\text{—}CH_2\text{—}X$$

wherein x is 0 to 20, inclusive and y is 0 to 20, inclusive, with the proviso that the total molecule not exceed about 30 carbon atoms. Preferably, x and y will each independently be integers of about 2 up to about 12.

With respect to the halide moiety, X can broadly be selected from Cl, Br, or I. Br is the presently preferred halide because of the excellent reactivity of the resulting organic halide compounds and the ready availability of organic bromides suitable for the practice of the present invention.

The first reaction step of the inventive process involves preheating of a preliminary mixture consisting essentially of organic halide and dimethyl sulfoxide, (DMSO). After a suitable preheating period has elapsed, sodium bicarbonate is added and the reaction mixture is then heated to oxidation reaction conditions. In accordance with a particular embodiment of the invention, cosolvent may optionally be added to the reaction mixture along with sodium bicarbonate prior to the second heating step. In accordance with another particular embodiment of the invention, the second heating step can be carried out under reduced pressure, i.e., less than atmospheric pressure. In accordance with yet another particular embodiment of the invention, the second heating step can be carried out under reduced presure and in the further presence of cosolvent.

With respect to the first step of the inventive process, i.e., the preheating step, it is desired that the organic halide and DMSO be contacted at sufficient temperature for sufficient time to allow the formation of an initial complex which is less prone to alcohol formation when sodium bicarbonate is added then if all reagents were blended at one time. In order to provide additional guidance, the following operating parameters are suggested:

|  | Temperature, °C. | Time, hr. |
|---|---|---|
| Broad | 40-100 | 0.1-12 |
| Intermediate | 50-75 | 0.2-2 |
| Preferred | 55-70 | 0.3-1 |

With respect to the second step of the inventive process, i.e., wherein a mixture consisting essentially of organic halide, DMSO and sodium bicarbonate are subjected to oxidation reaction conditions, the following reaction parameters are suggested:

|  | Temperature, °C. | Time, hr. |
|---|---|---|
| Broad | 90-180 | 0.1-12 |
| Intermediate | 110-150 | 0.2-4 |
| Preferred | 120-135 | 0.3-2 |

While the ratios of reagents employed are not believed to be critical, the following values are provided for guidance as to efficient use of materials and because good results have been obtained when reactions have been carried out within these ranges. All values presented below are expressed as molar ratios, based on the number of moles of organic halide employed in the oxidaton reaction.

|  | Reagent/Organic halide Mole ratio | | |
|---|---|---|---|
|  | Reagent = DMSO | $NaHCO_3$ | Cosolvent |
| Broad | 2-40:1 | 1-20:1 | 0.1-20:1 |
| Intermediate | 10-30:1 | 1-10:1 | 0.2-5:1 |
| Preferred | 15-25:1 | 1-5:1 | 0.3-3:1 |

The above ratios indicate that dimethylsulfoxide is always employed in greater than a molar excess with respect to the organic halide to be oxidized; thus, DMSO also functions as a reaction solvent, in addition to at least a portion of the DMSO participating in the oxidation reaction and being consumed thereby. When a second solvent is optionally employed, it is referred to herein as cosolvent.

When employed, cosolvent is added to the oxidation process of the present invention along with sodium bicarbonate prior to subjecting the reaction mixture to oxidation reaction conditions. As indicated above, the amount of cosolvent which may suitably be employed can vary widely. Suitable cosolvents are selected from the group consisting of:
dimethylphthalate,
triglyme,
caprolactone,
and mixtures of any two or more thereof.

When the second heating step is carried out under reduced pressure, any pressure less than atmospheric, i.e., 760 mm Hg, is suitable. Preferably, a reaction pressure of about 50-400 mm Hg will be employed, with pressures in the range of about 100-300 mm Hg most preferred for ease of operation and good results.

A further understanding of the present invention and its advantages will be provided by reference to the following non limiting examples.

EXAMPLE I

Run 1 (Control): Dimethyl sulfoxide (DMSO; 150 mL, 165 g, 2.1 mol) and sodium bicarbonate ($NaHCO_3$; 20 g, 0.24 mol) were heated to 130° C., then 11-hexadecenyl bromide (30 g, 0.1 mol) added rapidly with stirring. The mixture containing all three reagents, i.e. DMSO, $NaHCO_3$ and hexadecenyl bromide, was heated for 1 hour. The mixture was then cooled and filtered. GLC analysis indicated a selectivity to 11-hexadecenal of 68.1% and to hexadecenol of 24.8%, for an aldehyde/alcohol ratio of about 2.7:1.

EXAMPLE II

Oxidation of 11-Hexadecenyl Bromide

Run 2 (invention): Hexadecenyl bromide (30 g, 0.1 mol) and DMSO (150 mL, 165 g, 2.1 mol) were combined and heated to about 70° C. over about a 15 minute period. Once this original combination had reached 70° C., $NaHCO_3$ (20 g, 0.24 mol) was added and the reaction temperature increased to 130° C. and maintained at that temperature for 1 hour. The reaction mixture was then cooled and filtered. The lower layer (DMSO layer) was separated, extracted two times with 60 mL aliquots of hexane. The hexane extracts were combined with the upper (aldehyde) layer, and solvent removed in a rotary evaporator. GLC analysis of the reaction mixture indicated a selectivity to 11-hexadecenal of 73.5% and to hexadecenol of only 15.8%, for an aldehyde/alcohol ratio of about 4.7:1.

Run 3 (invention): The oxidation procedure employed for run 2 was repeated on a larger scale. Thus, 360 g (1.2 mol) of hexadecenyl bromide and 1800 mL (1980 g; 25.4 mol) of DMSO were mixed and heated to 60° C., with temperature maintained at 60° C. for about 30 minutes. Then, 240 g (2.9 mol) of $NaHCO_3$ was added and the temperature of the reaction mixture raised to 130° C., which was maintained for 2 hours. The reaction mixture was then cooled and filtered. The lower layer (DMSO layer) was separated and extracted with about 1 L of hexane. The hexane extract and upper (aldehyde) layer were combined, washed once with about 100 mL of water, then concentrated on a rotary evaporator. GLC analysis indicated an aldehyde/alcohol ratio of 4.5:1. A distilled yield of 38% Z-11-hexadecenal was obtained.

EXAMPLE III

Oxidation of 11-Hexadecenyl Bromide under Reduced Pressure

Run 4 (invention): The procedure employed for run 3 was repeated, except that upon addition of $NaHCO_3$, the reaction pressure was reduced to about 160-200 mm Hg. The reaction mixture was worked up as about and GLC analysis indicated an aldehyde/alcohol ratio of about 6.7:1. A distilled yield of 44% Z-11-hexadecenal was obtained.

It can be seen by comparing the results of runs 3 and 4 that a greater recovery of Z-11-hexadecenal by distillation is possible with high aldehyde/alcohol distillation feed ratios.

EXAMPLE IV

Oxidation of 11-Hexadecenyl Bromide in the Presence of Cosolvent

Hexadecenyl bromide (360 g; 1.2 mol) and 1800 mL (2660 g; 34 mol) of DMSO were mixed and heated to 60° C. for 30 minutes. Then, NaHCO$_3$ and a co-solvent were added, pressure reduced and temperature raised for the period of time specified in Table I. Reaction mixture was then cooled and concentrated on a rotary evaporator. GLC analysis was then carried out to determine aldehyde/alcohol ratios in the reaction product. Results from reactions employing several different co-solvents are summarized in Table I as runs 5-9.

Table II, for example), the co-solvents seem to be useful in the practice of the present invention are:
triglyme,
dimethylphthalate, and
caprolactone.

The examples have been provided merely to illustrate the practice of my invention and should not be read so as to limit the scope of my invention or the appended claims in any way. Reasonable variations and modifications, not departing from the essence and spirit of my invention, are contemplated to be within the scope of patent protection desired and sought.

That which is claimed:

1. A process for the conversion of organic halides to

TABLE I

|  |  | Reagents, mol |  |  | Reaction Conditions |  |  | Product Yield, % |  | Product |
|---|---|---|---|---|---|---|---|---|---|---|
| Run | Halide* | DMSO | NaHCO$_3$ | Co-solvent** | Time, h | Temp., °C. | Press, mm Hg | Aldehyde | Alcohol | Ratio*** |
| 1 (control) | 0.1 | 2.1 | 0.24 | none | 1 | 130 | 760 | 68.1 | 24.8 | 2.7 |
| 2 (invention) |  |  |  |  |  |  |  |  |  |  |
| step 1 | 0.1 | 2.1 |  | none | 0.25 | 70 | 760 |  |  |  |
| step 2 |  |  | 0.24 | none | 1 | 130 | 760 | 73.5 | 15.8 | 4.7 |
| 3 (invention) |  |  |  |  |  |  |  |  |  |  |
| step 1 | 1.2 | 25.4 |  | none | 0.5 | 60 | 760 |  |  |  |
| step 2 |  |  | 2.9 | none | 2 | 130 | 760 | ND**** | ND | 4.5 |
| 4 (invention) |  |  |  |  |  |  |  |  |  |  |
| step 1 | 1.2 | 25.4 |  | none | 0.5 | 60 | 760 |  |  |  |
| step 2 |  |  | 2.9 | none | 2 | 130 | 160-200 | 67.8 | 10.1 | 6.7 |
| 5 (invention) |  |  |  |  |  |  |  |  |  |  |
| step 1 | 1.2 | 25.4 |  | none | 0.5 | 60 | 760 |  |  |  |
| step 2 |  |  | 2.9 | TG, 1.0 | 3 | 120 | 120 | ND | ND | 7.0 |
| 6 (invention) |  |  |  |  |  |  |  |  |  |  |
| step 1 | 1.2 | 25.4 |  | none | 0.5 | 60 | 760 |  |  |  |
| step 2 |  |  | 2.4 | DMP, 2.2 | 2 | 120 | 120 | 63.0 | 6.4 | 9.8 |
| 7 (invention) |  |  |  |  |  |  |  |  |  |  |
| step 1 | 1.2 | 25.4 |  | none | 0.5 | 60 | 760 |  |  |  |
| step 2 |  |  | 2.4 | DMP, 2.2 | 1 | 120 | 120 | 63.3 | 4.5 | 14.1 |
| 8 (invention) |  |  |  |  |  |  |  |  |  |  |
| step 1 | 1.2 | 25.4 |  | none | 0.5 | 60 | 760 |  |  |  |
| step 2 |  |  | 2.9 | CL, 3.2 | 2 | 120 | 120 | 64.5 | 6.8 | 9.5 |
| 9 (comparison) |  |  |  |  |  |  |  |  |  |  |
| step 1 | 1.2 | 25.4 |  | none | 0.5 | 60 | 760 |  |  |  |
| step 2 |  |  | 4.3 | BL, 4.7 | 2 | 125 | 120 | ND | ND | 8.4 |

*Halide = 11-hexadecenyl bromide
**Co-solvent:
TG = triglyne(triethylene glycol dimethyl ether)
DMP = dimethyl phthalate
CL = caprolactone
BL = butyrolactone
***Product ratio = aldehyde/alcohol ratio
****ND = not determined It can be seen that the use of co-solvent in all runs gives an improved aldehyde/acohol ratio compared to reactions carried out with no added co-solvent. When the reaction mixtures were further purified by distillation, however, a substantial variation in product aldehyde recovery was observed:

TABLE II

Distillation Yields of 11-Hexadecenal

| Run | Co-solvent employed | Aldehyde/Alcohol | Distilled Yield, % |
|---|---|---|---|
| 3 | none | 4.5 | 38 |
| 4 | none | 6.7 | 44 |
| 5 | triglyme | 7.0 | 47 |
| 6 | dimethyl phthalate | 9.8 | 51 |
| 7 | dimethyl phthalate | 14.1 | 46 |
| 8 | caprolactone | 9.5 | 49 |
| 9 | butyrolactone | 8.4 | 38 |

Since an improvement of aldehyde/alcohol ratio is of little value where the yield of the desired product (i.e. aldehyde) is not improved (compare runs 3 and 9 in organic aldehydes wherein the organic halides have the formula:

$$RCH_2-X$$ 

wherein R is a $C_3$–$C_{30}$ organic radical and X is selected from the group consisting of Cl, Br and I, said process comprising:

(a) heating a mixture of said organic halide and dimethylsulfoxide (DMSO) to a temperature in the range of about 40° C. to 100° C. for a time in the range of about 0.1 to 12 hours, then (b) adding at least one mole of sodium bicarbonate per mole of organic halide to the result of step (a) and thereafter (c) heating the sodium bicarbonate containing mixture to a temperature in the range of about 90° C. to 180° C. for a time in the range of about 0.1 to 12 hours.

2. A process in accordance with claim 1 wherein the mole ratio of DMSO to organic halide is at least about 2:1 and no greater than about 40:1.

3. A process in accordance with claim 1 wherein X is bromine.

4. A process in accordance with claim 1 wherein said organic halide has the structure:

$$H-(CH_2)_x-CH=CH-(CH_2)_y-CH_2-X$$

wherein x is 0–20, inclusive and y is 0–20, inclusive, with the proviso that the total molecule not exceed 30 carbon atoms.

5. A process in accordance with claim 4 wherein the double bond of said organic halide is a cis double bond.

6. A process in accordance with claim 5 wherein x is 9 and y is 4.

7. A process in accordance with claim 1 wherein step (b) further comprises adding at least one cosolvent selected from the group consisting of:
dimethylphthalate,
triglyme,
caprolactone,
and mixtures of any two or more thereof to the result of step (a).

8. A process in accordance with claim 7 wherein the mole ratio of cosolvent to organic halide is at least about 0.1:1 and no greater than about 20:1.

9. A process in accordance with claim 1 wherein step (b) is carried out at less than atmospheric pressure.

10. A process in accordance with claim 7 wherein step (b) is carried out at less than atmospheric pressure.

* * * * *